(12) United States Patent
Chung

(10) Patent No.: US 6,322,529 B1
(45) Date of Patent: Nov. 27, 2001

(54) DETACHMENT TYPE WAIST PROTECTING BELT

(76) Inventor: Joon Young Chung, Woosung Apt. 27-1506, 101 Jamsil-dong, Songpa-ku, Seoul (KR)

( * ) Notice: Subject to any disclaimer, the term of this patent is extended or adjusted under 35 U.S.C. 154(b) by 0 days.

(21) Appl. No.: 09/695,159

(22) Filed: Oct. 24, 2000

(51) Int. Cl.7 .............................. A61F 5/00; A41F 19/00
(52) U.S. Cl. ........................... 602/19; 2/467; 2/319
(58) Field of Search ............................. 2/467, 455, 44, 2/45, 338, 310, 237, 311, 312, 920; 128/99.1–102.1, 875, 876, DIG. 15, 869; 602/19, 23

(56) References Cited

U.S. PATENT DOCUMENTS

| | | | |
|---|---|---|---|
| 2,554,337 | * 5/1951 | Lampert ................................. | 128/96 |
| 4,022,197 | 5/1977 | Castiglia . | |
| 4,508,110 | * 4/1985 | Modglin ................................. | 128/78 |
| 4,640,269 | * 2/1987 | Goins ..................................... | 128/78 |
| 4,964,401 | 10/1990 | Taigen . | |
| 5,158,098 | 10/1992 | Jalalian . | |
| 5,309,926 | 5/1994 | Mayton . | |
| 5,310,401 | * 5/1994 | Striano ................................... | 602/19 |
| 5,316,022 | 5/1994 | Schiek, Sr. . | |
| 5,363,863 | * 11/1994 | Lelli et al. ........................... | 128/876 |
| 5,407,422 | 4/1995 | Matthijs et al. . | |
| 5,984,885 | * 11/1999 | Gaylort et al. ........................ | 602/19 |
| 6,190,343 | * 2/2001 | Heinz et al. ........................... | 602/19 |
| 6,213,968 | * 4/2001 | Heinz et al. ........................... | 602/19 |

* cited by examiner

Primary Examiner—John J. Calvert
Assistant Examiner—Tejash Patel
(74) Attorney, Agent, or Firm—Needle & Rosenberg PC

(57) ABSTRACT

Disclosed is a detachment type waist protecting belt wherein hook and loop fastener strips are attached to distal ends and heightwise middle portions of left and right bands, a pair of connecting plates made of a soft plastic material are secured to proximal ends of the left and right bands, connection rings are rotatably fastened to the connecting plates by pins to be spaced one from another in a longitudinal direction by a predetermined distance, both ends of a pair of pulling cords respectively pass zigzag from upper and lower ends of the connecting plates through the connection rings so as to be freed at heightwise middle portions of the connecting plates, and a pair of tightening bands are connected to the freed both ends of the pulling cords. The detachment type waist protecting belt includes a waist support which fits a contour of the waist of the human body. Guide projections are formed at both sides of an outer surface of the waist support. The heightwise middle portions of the left and right bands are defined with guide slots which extend in a transverse direction to guide the guide projections, whereby the detachment type waist protecting belt can be equipped with the waist support as occasion arises.

3 Claims, 7 Drawing Sheets

(a)

(b)

(a)

(b)

DETACHMENT TYPE WAIST PROTECTING BELT

BACKGROUND OF THE INVENTION

1. Field of the Invention

The present invention relates to a detachment type waist protecting belt, and more particularly, the present invention relates to a detachment type waist protecting belt which is provided with a waist support in a manner such that the waist support can be attached to the waist protecting belt to be integrally used therewith or can be detached from the waist protecting belt to enable the waist protecting belt to be independently used, as occasion demands.

2. Description of the Related Art

As well known in the art, a waist protecting belt is also call an abdominal support or a pelvic girdle. Generally, the waist protecting belt is formed to have a substantial width using a proper material such as spandex. By providing a buckle or a fastener element such as Velcro-brand hook and loop fastener strips to the waist protecting belt, the waist protecting belt can be worn around the waist. The waist protecting belt serves to compress to some degree and widely support the waist of the human body, thereby maintaining the waist in substantially a straightened state and not causing a pain.

Due to the fact that the conventional waist protecting belt is made of a material having a predetermined contractibility, the conventional waist protecting belt is-suitable for a pregnant woman or a person having a stickingout stomach. However, in the case of a patient associated with the vertebra or the intervertebral disk, because it is necessary to maintain the waist in an exactly straightened state, the waist protecting belt which is made of a material such as spandex having a predetermined contractibility, is not suitable for the patient associated with the vertebra or the intervertebral disk. In particular, since the conventional waist protecting belt is constructed in a manner such that it is tightened only in a front part, in order to strictly straightly support the waist, a waist protecting belt configured in such a way as to be capable of being tightened in a rear part as well and thereby widely supporting a region including the vertebra and the waist, is demanded.

To cope with these problems, a waist protecting belt is disclosed in Korean Utility Model Application No. 96-50629 which was filed in the name of the present applicant. That is to say, as shown in FIG. 1, the waist protecting belt includes left and right bands 10 and 20. Velcro-brand hook and loop fastener strips 11 and 21 are attached to distal ends and heightwise middle portions of the left and right bands 10 and 20. A plurality of locking projections 13 and 23 having circumferential engaging grooves 12 and 22 are arranged on proximal ends of the left and right bands 10 and 20. The waist tightening belt further includes a rear tightening arrangement 30. The rear tightening arrangement 30 has a pair of connecting plates 30 and 30'. The pair of connecting plates 31 and 31' are defined with a plurality of locking holes into which the locking projections 13 and 23 are respectively engaged. The pair of connecting plates 31 and 31' are formed with a plurality of projected shaft portions around which a plurality of rollers are respectively fitted in a manner such that the rollers can be idly rotated. A pulling cord 37 is wound zigzag around the rollers. Both ends 38 and 38' of the pulling cord 37 which both ends are freed from a center portion of one connecting plate 31', are connected to a tightening band 40. By the above-described construction, due to the fact that a user can selectively tighten the waist protecting belt at a rear part thereof, convenience is rendered upon using the waist protecting belt. However, by the fact that the pair of connecting plates which actually serve to support the waist, are made of a hard material, since the pair of connecting plates cannot be brought into close contact with the waist which is always concaved inward when considering the structure of the human body, the connecting plates can adversely affect the waist, whereby an effect afforded by the waist protecting belt can be deteriorated. Also, because means for tightening the left and right bands comprises costly rollers, a manufacturing cost is increased.

To solve these drawbacks which are provoked in the waist protecting belt described in Korean Utility Model Application No. 96-50629, another waist protecting belt is disclosed in Korean Utility Model Application No. 2000-14844 which was also filed in the name of the present applicant. Namely, as shown in FIG. 2, the waist protecting belt includes left and right bands 101 and 102. Velcro-brand hook and loop fastener strips 103 are attached to distal ends and a heightwise middle portions of the left and right bands 101 and 102. A pair of connecting plates 105 and 106 are secured to proximal ends of the left and right bands 101 and 102 to be positioned in a longitudinal direction. Both ends of a pair of pulling cords 107 pass zigzag from upper and lower ends of and through the connecting plates 105 and 106 so as to be freed at heightwise middle portions of the connecting plates 105 and 106. The both ends of the pair of pulling cords 107 pass through the connecting plates 105 and 106 at places which are spaced apart one from another by a predetermined distance in the longitudinal direction. A pair of tightening bands 108 and 109 are connected to the freed both ends of the pair of pulling cords 107. In the waist protecting belt, the connecting plates 105 and 106 are made of a soft plastic material and are respectively stitched to the left and right bands 101 and 102. A plurality of connection rings 110 are rotatably fastened to the connecting plates 105 and 106 by pins 110a in such a way as to be spaced one from another in the longitudinal direction by the predetermined distance. The both ends of the pair of pulling cords 107 pass zigzag through the plurality of connection rings 110 and are freed through two pairs of connection rings 110 which are positioned at center portions of the connecting plates 105 and 106 so as to be respectively connected to the pair of tightening bands 108 and 109. The proximal ends of the left and right hands 101 and 102 to which the connecting plates 105 and 106 are fastened, are configured in a manner such that each of their upper waist supporting portions 111 has a length which is greater than that of each of their lower hip supporting portions 112. In the waist protecting belt constructed as mentioned above, because the connecting plates 105 and 106 which actually serve to support the waist, are made of the soft plastic material, the waist protecting belt can be curved in conformity with a contour of the waist of the human body. Also, since the connection rings 110 can be rotated about the pins 110a, the connecting plates 105 and 106 can be maximally brought into close contact with the waist. Moreover, due to the fact that the upper waist supporting portion 111 has a length which is greater than that of the lower hip supporting portion 112, it is possible to widely support a region including the vertebra and the waist in a more reliable manner when compared to the waist protecting belt described in Korean Utility Model Application No. 96-50629.

However, the waist protecting belt described in Korean Utility Model Application No. 2000-14844, constructed as mentioned above, is still encountered with defects in that, since the connection ring can be rotated about the pin by an angle of 360°, when keeping the waist protecting belt, the connection ring can be rotated rearward in such a way as to cause the pulling cord to be entangled, whereby inconvenience is induced upon using the waist protecting belt. Also, even though the connecting plates are made of a soft plastic material, because a flexibility is not so high that it is difficult to cause the connecting plates to be curved in conformity with the contour of the waist of the human body.

Furthermore, as patients associated with the vertebra or the intervertebral disk have a variety of conditions, in the case of a patient who is in a serious condition, it is necessary to widely support a region including the back and the waist using a hard type waist support such as a chair back brace, thereby to fixedly maintain in a straightened state and protect the vertebra. Then, as the condition of the patient takes a turn for the better, a waist protecting belt can be independently used. In this regard, while the waist protecting belt described in Korean Utility Model Application No. 2000-14844 is suitable for a patient whose condition takes a turn for the better, it cannot be reliably applied to a patient who is in a serious condition.

SUMMARY OF THE INVENTION

Accordingly, the present invention has been made in an effort to solve the problems occurring in the related art, and an object of the present invention is to provide a detachment type waist protecting belt which is provided with a hard type waist support for a vertebra-related patient in a manner such that the waist support can be attached to the waist protecting belt to be integrally used therewith in the case of a serious vertebra-related patient or can be detached from the waist protecting belt to enable the waist protecting belt to be independently used in the case of a vertebra-related patient who takes a turn for the better, whereby applicability of the waist protecting belt can be expanded.

Another object of the present invention is to provide a detachment type waist protecting belt which limits rotation of connection rings to a predetermined angle while not being adversely affected in terms of its use, so as to prevent pulling cords from being entangled, thereby improving convenience upon its use, and in which each of connecting plates is configured in such a way as to define a wavelike figure, thereby improving flexibility of the connecting plate.

In order to achieve the above objects, according to one aspect of the present invention, there is provided a detachment type waist protecting belt wherein Velcro-brand hook and loop fastener strips are attached to distal ends and heightwise middle portions of left and right bands, a pair of connecting plates made of a soft plastic material are secured to proximal ends of the left and right bands, a plurality of connection rings are rotatably fastened to the connecting plates by pins in such a way as to be spaced one from another in a longitudinal direction by a predetermined distance, both ends of a pair of pulling cords respectively pass zigzag from upper and lower ends of the connecting plates through the connection rings so as to be freed at heightwise middle portions of the connecting plates, and a pair of tightening bands are connected to the freed both ends of the pair of pulling cords, characterized in that the detachment type waist protecting belt includes a hard type waist support which has a U-shaped cross-section and which fits a contour of the waist of the human body, guide projections are formed at both sides of an outer surface of the waist support, and the heightwise middle portions of the left and right bands are defined with guide slots which extend in a transverse direction to guide the guide projections, whereby the detachment type waist protecting belt can be equipped with the waist support as occasion arises.

According to another aspect of the present invention, the guide projections are formed in a manner such that they are arranged in line along a horizontal direction and each of them has a head portion and a shaft portion, and circular holes are defined at predetermined locations along the guide slots in a manner such that head portions of the guide projections can be inserted therethrough.

According to still another aspect of the present the connecting plates are defined, at places where the connection rings are fastened thereto, with first grooves, a pair of cover members are respectively fastened to the pair connecting plates and are defined, at places which correspond to the first grooves of the connecting plates, with second grooves, and each first groove and each corresponding second groove cooperate with each other so as to accommodate a portion of the connection ring in a space created therebetween and limit rotation of the connection ring to a predetermined angle; wherein opposite surface of the connecting plates and the cover members are waved in such a way as to have a pitch substantially corresponding to the predetermined distance and thereby are rendered flexible to be optimally fitted the contour of the waist of the human body; and wherein guide rollers each having a circumferential groove are interposed between the connecting plates and the cover members at positions where the both ends of the pulling cords are freed through the connecting plates and the cover members, and guide pieces each having a predetermined height are formed on the cover members in a manner such that they guide the freed both ends of pulling cords toward the distal ends of the left and right bands.

BRIEF DESCRIPTION OF THE DRAWINGS

The above objects, and other features and advantages of the present invention will become more apparent after a reading of the following detailed description when taken in conjunction with the drawings, in which:

FIGS. 5(a) and 5(b) are respectively partial enlarged perspective view and front view, wherein FIG. 5(a) illustrates a connection ring a portion of which is accommodated in grooves defined in a connecting plate and a cover member and FIG. 5(b) illustrates a rotation limiting principle for the connection ring;

DETAILED DESCRIPTION OF PREFERRED EMBODIMENTS

Figure 1:
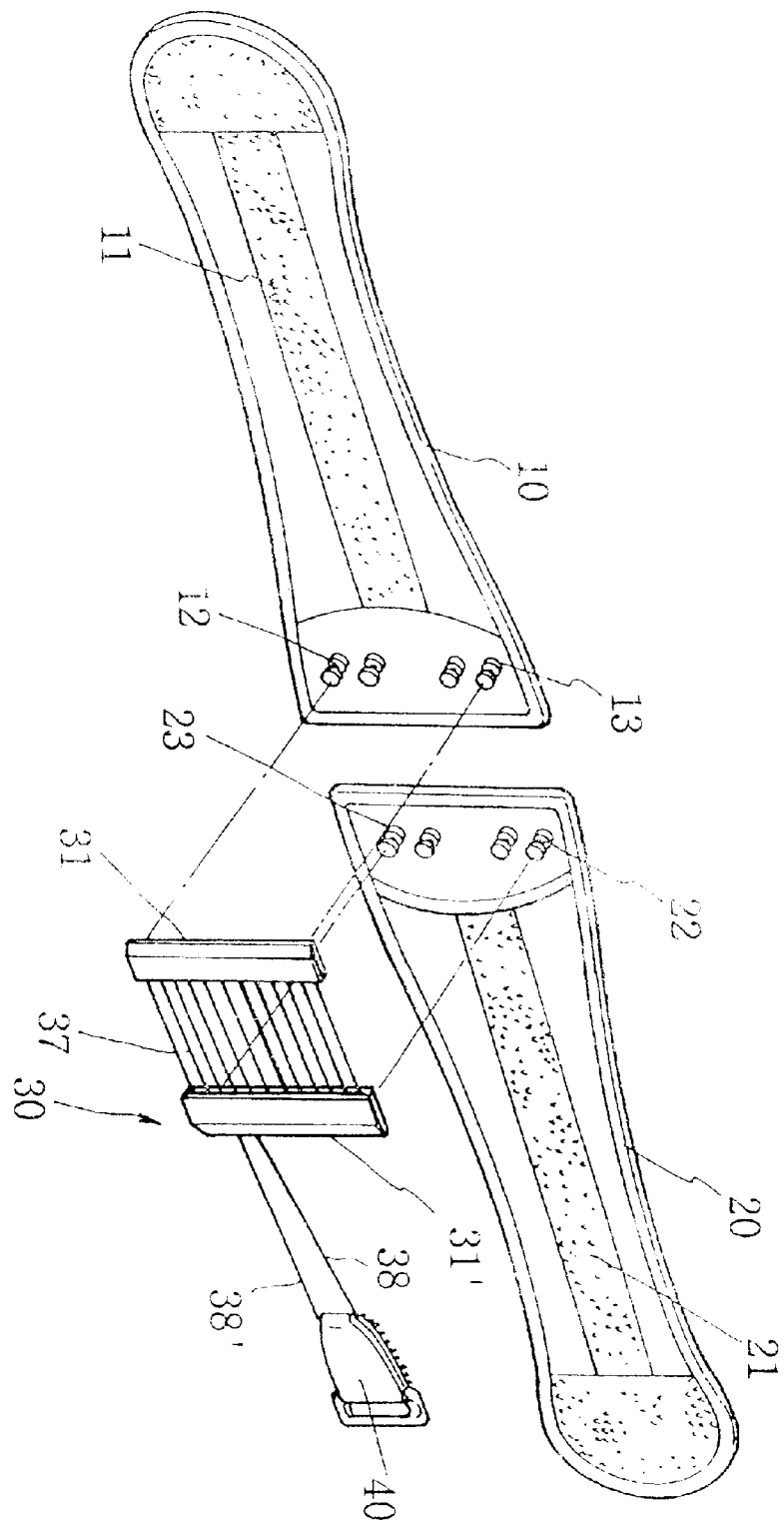
FIG. 1 is an exploded perspective view illustrating a conventional waist protecting belt.
Figure 2:
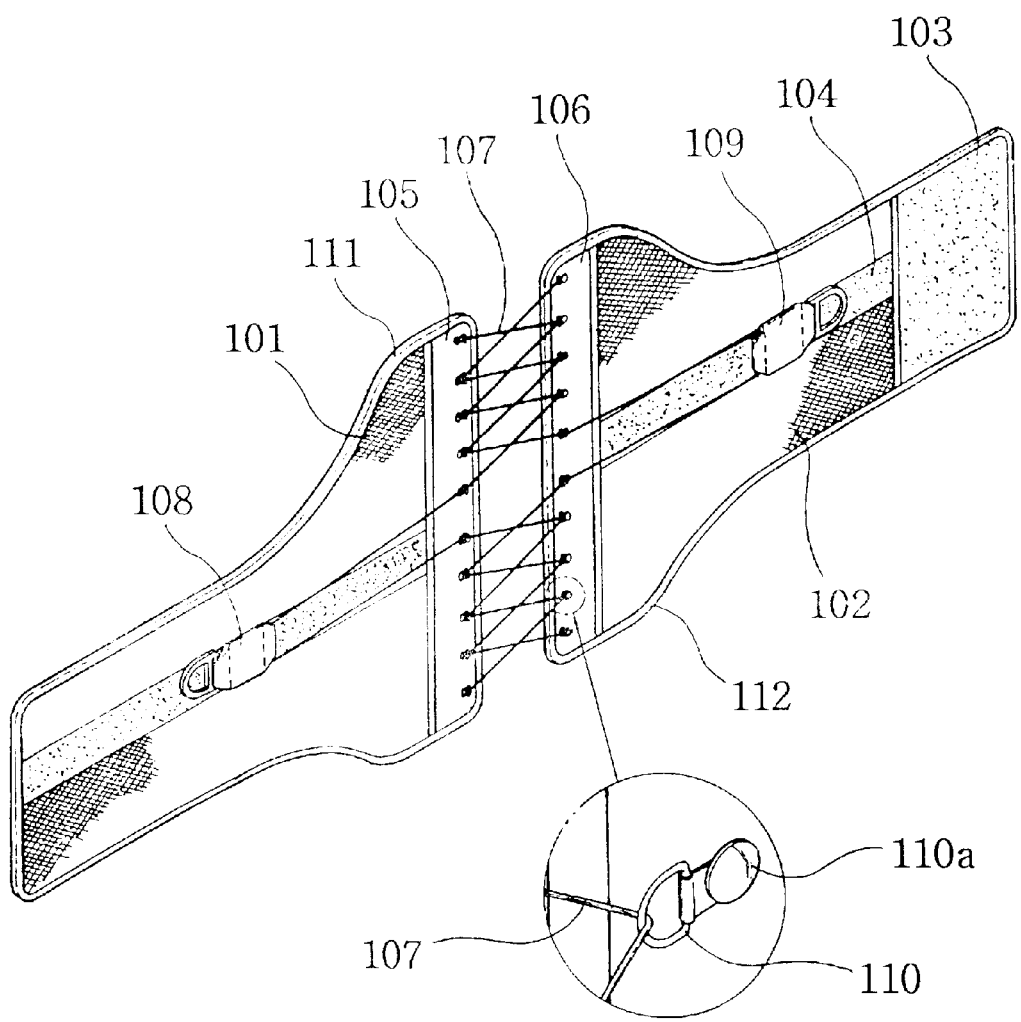
FIG. 2 is a partially enlarged perspective view illustrating another conventional waist protecting belt.

Reference will now be made in greater detail to a preferred embodiment of the invention, an example of which is illustrated in the accompanying drawings. Wherever possible, the same reference numerals will be used throughout the drawings and the description to refer to the same or like parts.

Figure 3:
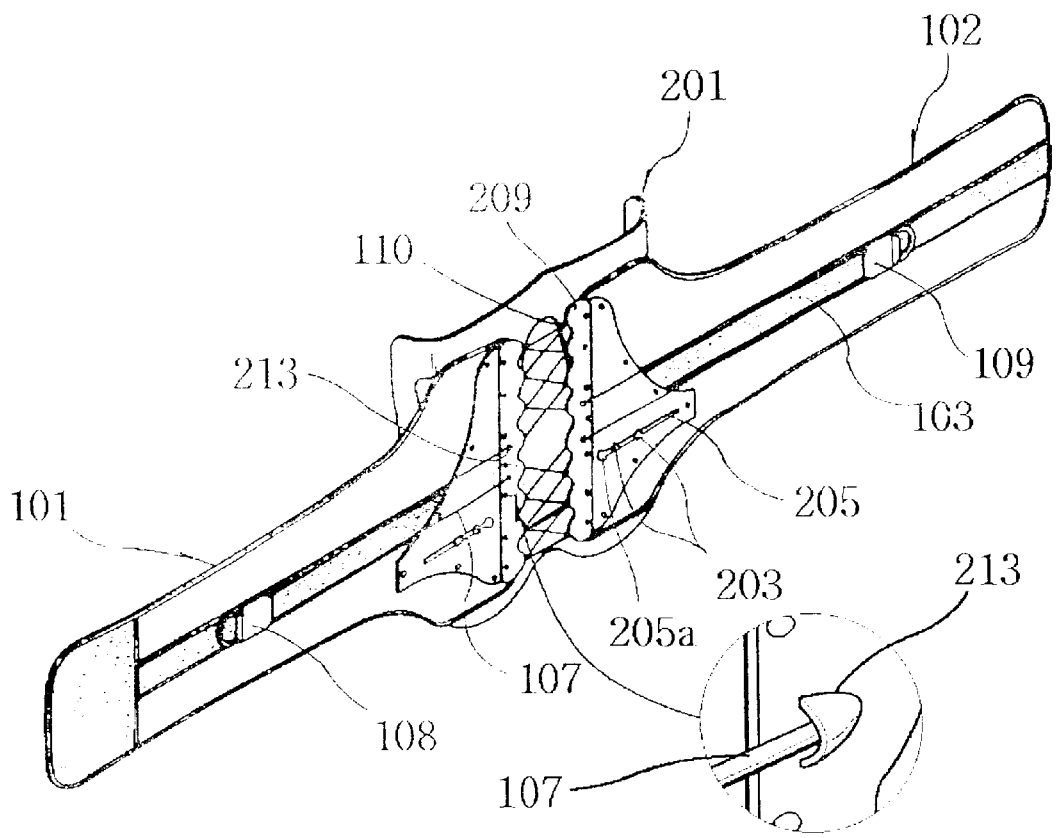
FIG. 3 is a partially enlarged perspective view illustrating a detachment type waist protecting belt in accordance with an embodiment of the present invention.
Figure 4:
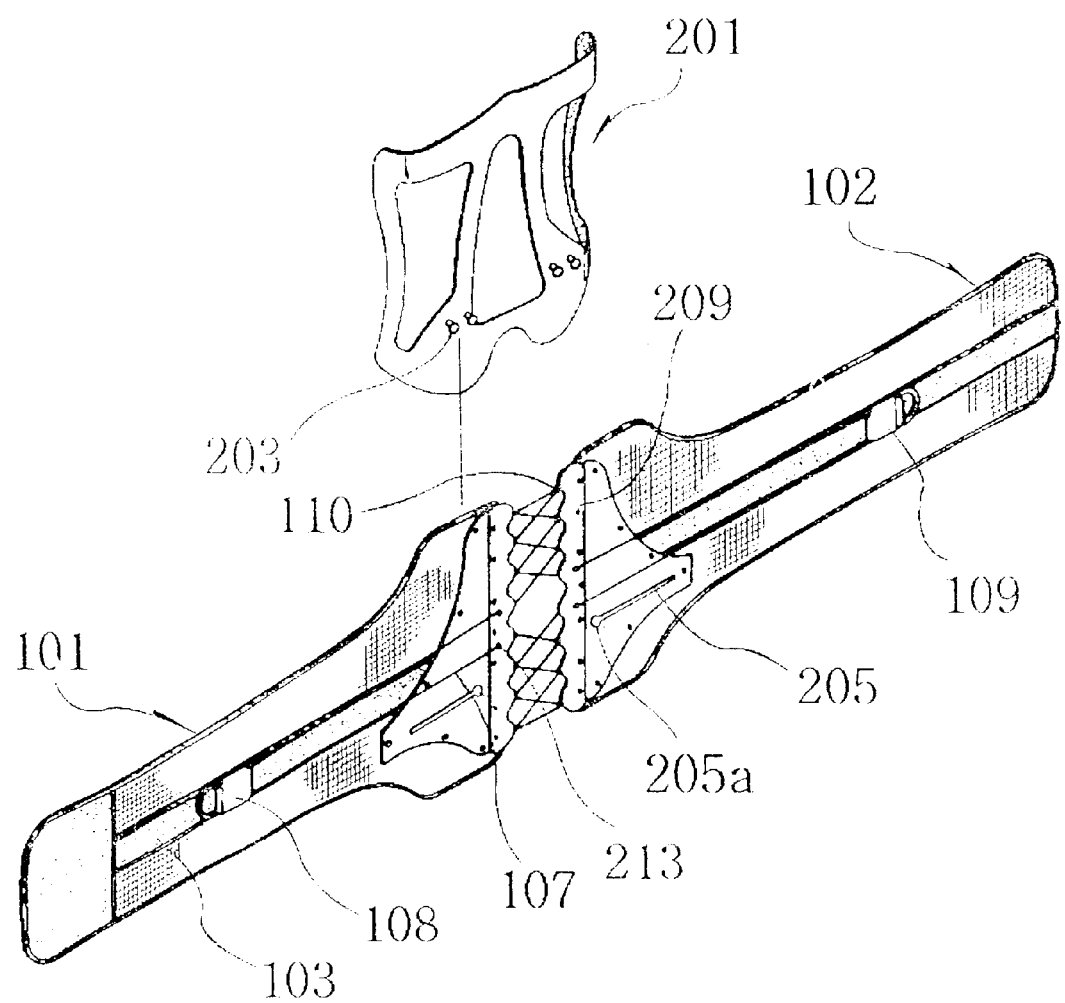
FIG. 4 is a perspective view illustrating a state wherein a waist support is detached from the waist protecting belt according to the present invention.
Figure 5:
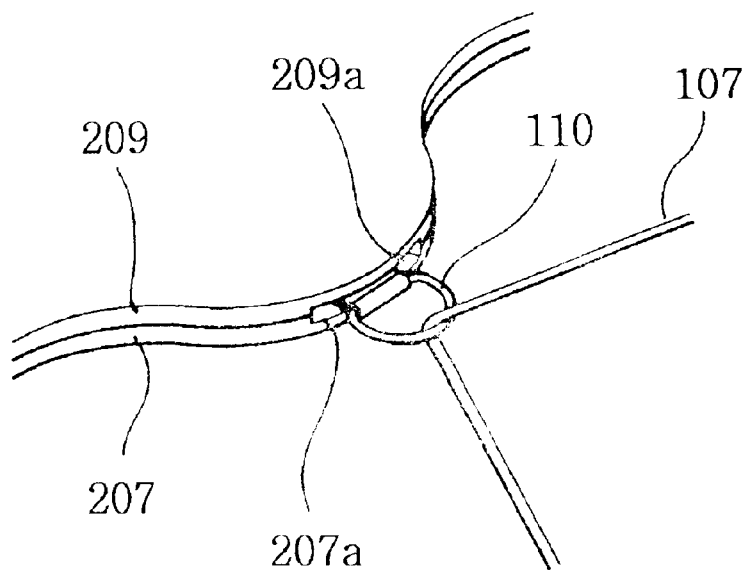
Figure 5:
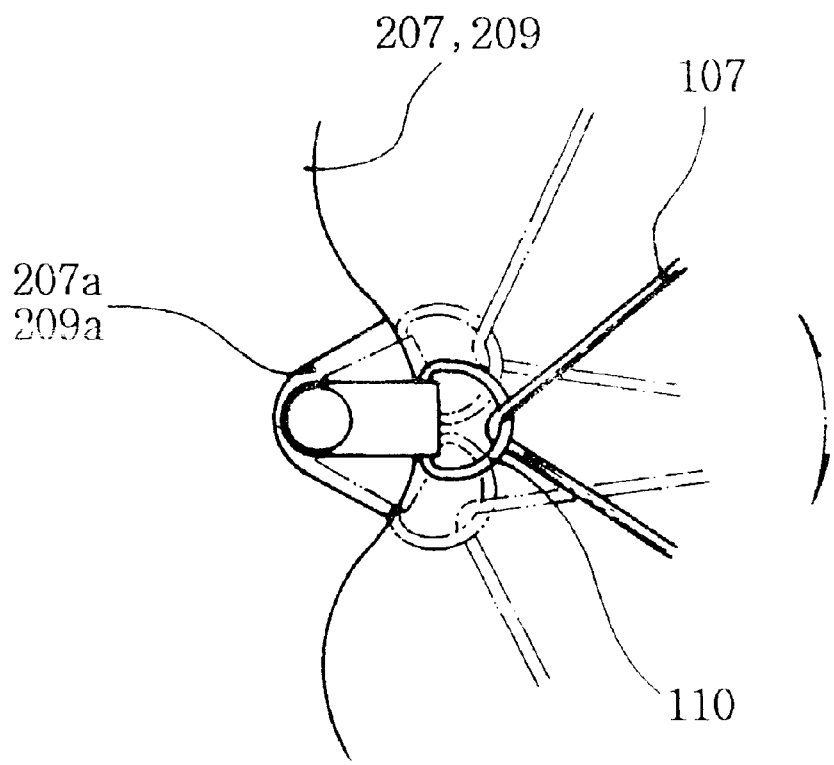

FIG. 3 is a partially enlarged perspective view illustrating a detachment type waist protecting belt in accordance with an embodiment of the present invention; and FIG. 4 is a perspective view illustrating a state wherein a waist support is detached from the waist protecting belt according to the present invention. As can be readily seen from FIGS. 3 and 4, in the present invention, a waist support for holding a vertebra region of a vertebra-related patient, including the back and waist, straightened, is separately configured to be selectively attached to or detached from the detachment type waist protecting belt according to the present invention. As described in Korean Utility Model Application No. 2000-14844, Velcro-brand hook and loop fastener strips 103 are attached to distal ends and heightwise middle portions of left and right bands 101 and 102, a pair of connecting plates 207 which are made of a soft plastic material such as polyethylene, are secured to proximal ends of the left and right bands 101 and 102, a plurality of connection rings 110 are rotatably fastened to the connecting plates 207 by pins in such a way as to be spaced one from another in a longitudinal direction by a predetermined distance, both ends of a pair of pulling cords 107 respectively pass zigzag from upper and lower ends of the connecting plates 207 through the connection rings 110 so as to be freed at heightwise middle portions of the connecting plates 207, and a pair of tightening bands 108 and 109 are connected to the freed both ends of the pair of pulling cords 107. According to the present invention, the detachment type waist protecting belt separately includes a rigid waist support 201 which has a Ushaped cross-section and which fits a contour of the waist of the human body, guide projections 203 are projectedly formed at both sides of an outer surface of the waist support 201, and the heightwise middle portions of the left and right bands 101 and 102 are defined with guide slots 205 which extend in a transverse direction to guide the guide projections 203, whereby the detachment type waist protecting belt can be equipped with the waist support 201 as occasion arises. The guide projections 203 are formed in a manner such that they are arranged in line along a horizontal direction. Each of the guide projections 203 has a head portion and a shaft portion so that the guide projection 203 is not easily removed from the guide slot 205 and a guide direction for the guide projection 203 is maintained. Circular holes 205a are defined at predetermined locations along the guide slots 205 in a manner such that the head portions of the guide projections 203 can be inserted therethrough.

Also, the connecting plates 207 are defined, at places where the connection rings 110 are fastened thereto, with first grooves 207a. A pair of cover members 209 are respectively fastened to the pair connecting plates 207 and are defined, at places which correspond to the first grooves 207a of the connecting plates 207, with second grooves 209a. Each first groove 207a and each corresponding second groove D 209a cooperate with each other so as to accommodate a portion of the connection ring 110 in a space created therebetween and to allow the connection ring 110 to be rotated therein thereby to limit rotation of the connection ring 110 to a predetermined angle. The connecting plates 207 and the cover members 209 are waved in such a way as to have a pitch substantially corresponding to the predetermined distance and thereby are rendered flexible to be optimally fitted the contour of the waist of the human body. Guide rollers 211 each having a circumferential groove 211a are interposed between the connecting plates 207 and the cover members 209 at positions where the both ends of the pulling cords 107 are freed through the connecting plates 207 and the cover members 209. Guide pieces 213 each having a predetermined height are formed on the cover members 209 in a manner such that they guide the freed both ends of pulling cords 107 toward the distal ends of the left and right bands 101 and 102.

Hereinafter, operations of the detachment type waist protecting belt according to the present invention, constructed as mentioned above, will be described in detail.

As described above, in the present invention, the waist support 201 for holding a vertebra region of a vertebra-related patient, including the back and waist, straightened, is separately configured to be selectively attached to or detached from the detachment type waist protecting belt according to the present invention. First describing operations of the waist protecting belt when the waist support 201 is detached from the waist protecting belt, the waist protecting belt is first positioned around the waist of a patient. By pulling the left and right bands 101 and 102 toward each other and attaching the Velcro-brand hook and loop fastener strips 103 to each other, the left and right bands 101 and 102 are primarily fastened to each other. Then, by pulling the tightening bands 108 and 109 in opposite directions from each other, the both ends of the pulling cords 107 are pulled leftward and rightward of the connecting plates 207. At this time, due to the fact that the both ends of the pulling cords 107 respectively pass zigzag from the upper and lower ends of the connecting plates 207 through the connection rings 110 which are rotatably fastened to the connecting plates 207 by the pins in such a way as to be spaced one from another in the longitudinal direction by the predetermined distance, as the both ends of the pulling cords 107 are pulled leftward and rightward of the connecting plates 207, a distance between the connecting plates 207 can be shortened, and thereby, the entire waist protecting belt can be tightened at a rear part thereof.

At this time, because the connecting plates 207 and the cover members 209 according to the present invention are made of a soft plastic material and opposite surfaces of the connecting plates 207 and the cover members 209 are waved to be repeatedly increased and decreased from top to bottom in a unit area, as the tightening bands 108 and 109 are tightened, the connecting plates 207 and the cover members 209 can be easily deformed in conformity with the contour of the waist of the human body thereby to be brought into close contact with the waist. In particular, by the fact that the connection rings 110 for connecting zigzag the pulling cords 107 to the connecting plates 207 are rotatably fastened to the connecting plates 207 by the pins, when the connecting plates 207 are brought into close contact with the waist of the human body, depending upon an input side angle and an output side angle of the pulling cords 107 which angles can be changed by bending of the pulling cords 107, the connection rings 110 can be adequately rotated to increase contactability of the connecting plates 207 with the waist.

Figure 6:
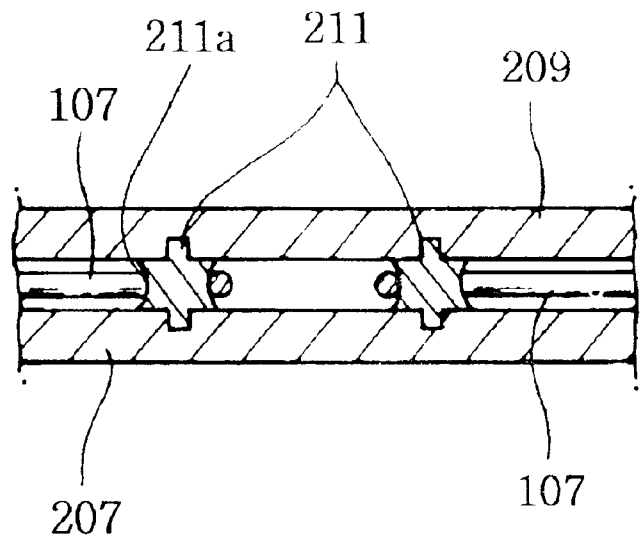
FIGS. 6(a) and 6(b) are respectively a cross-sectional view and a perspective view, illustrating guide rollers used in the detachment type waist protecting belt according to the present invention.
Figure 6:
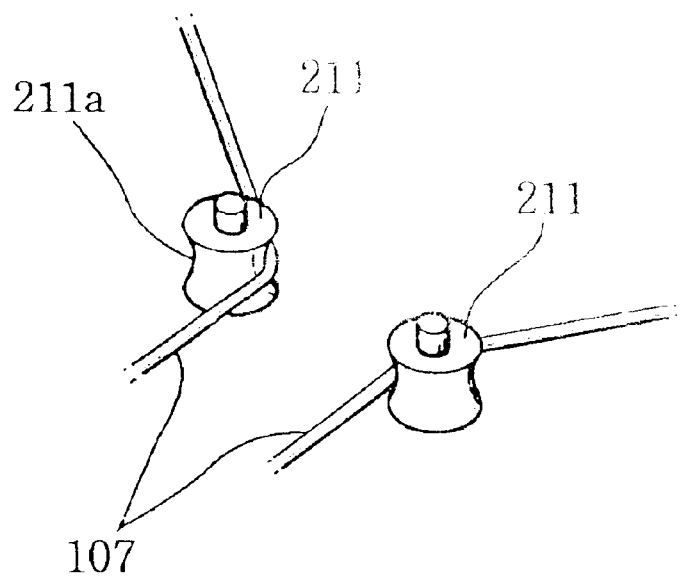
Figure 7:
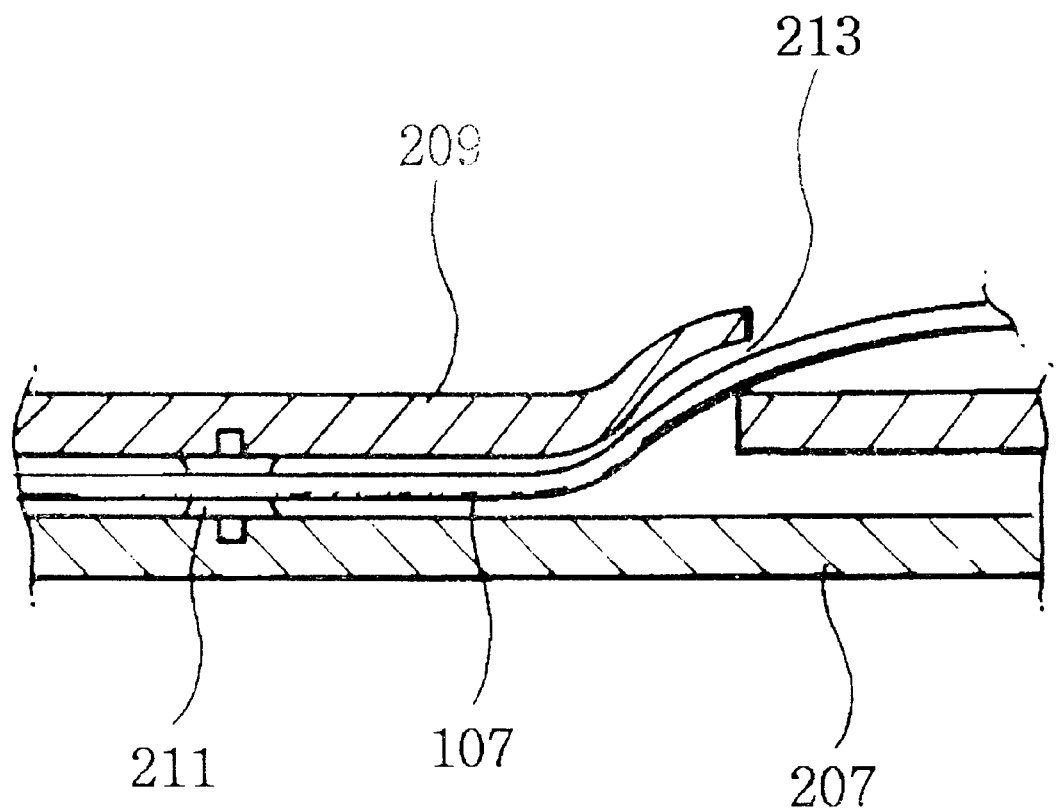
FIG. 7 is a cross-sectional view illustrating how both ends of pulling cords are freed through the connecting plate and the cover member.

Also, as shown in FIGS. 6 and 7, due to the fact that the guide rollers 211 each having the circumferential groove 211a are interposed between the connecting plates 207 and the cover members 209 at the positions where the both ends of the pulling cords 107 are freed through the connecting plates 207 and the cover members 209 and the guide pieces 213 each of which has a predetermined height and which are opened toward the distal ends of the left and right bands 101 and 102, that is, toward pulling directions of the pulling cords 107, are formed on the cover members 209 at the positions where the both ends of the pulling cords 207 are freed through the cover members 209, even though the user pulls the pulling cords 107 at any angles, each pair of pulling cords 107 can be uniformly pulled while defining substantially a parallel configuration, whereby the pulling cords 107 can be easily pulled out and load applied to the pulling cords 107 can be dispersed thereby to lengthen a lifetime of the pulling cords 107.

Further, due to the fact that each of the connection rings 110 of the waist protecting belt according to the present invention is accommodated in the space which is defined by the first and second grooves 207a and 209a when the connecting plate 207 and the cover member 209 are coupled with each other, it is possible to provide a sufficient rotation angle of the connection ring 110 when waist protecting belt is worn around the waist of the user. Also, as shown in FIG. 6, because the rotation angle of the connection ring 110 is limited to the predetermined angle by the first and second grooves 207a and 209a and therefore the connection ring 110 cannot be rotated by an angle of 360°, when keeping the waist protecting belt, the pulling cords 107 are prevented from being entangled due to the rotation of the connection rings 110, whereby user convenience is ensured.

After the user pulls the tightening bands 108 and 109 leftward and rightward to tighten the pulling cords 107 to a desired level, by attaching the Velcro-brand hook and loop fastener strips of the tightening bands 108 and 109 to the Velcro-brand hook and loop fastener strips 103 extending in the transverse direction, wearing of the waist protecting belt according to the present invention is completed. By this, the connecting plates 207 of the waist protecting belt can be deformed in conformity with the contour of the waist of the human body to be brought into close contact with the waist, whereby it is possible to most conveniently support the waist.

In the meanwhile, the separate hard type waist support 201 is provided to the waist protecting belt according to the present invention in such a way as to be selectively attached to and detached from the waist protecting belt. When a condition of a vertebra-related patient is serious, the waist support 201 can be attached to the waist protecting belt to be simultaneously used therewith.

In other words, when the waist protecting belt is used in a state wherein the waist support 201 is attached thereto, the guide projections 203 which are formed on the outer surface of the waist support 201, are fitted into the guide slots 205, and then, after supporting the vertebra region including the back and waist by a concaved portion of the waist support 201, the left and right bands 101 and 102 which constitute the waist protecting belt, are tightened as described above. According to this, left and right sides of the waist support 201 can be securely maintained by the tightening force of the waist protecting belt and thereby, can be brought into close contact with the waist of the human body. Accordingly, the waist support 201 can maintain the vertebra region including the back and waist in the straightened state while not being bent in the longitudinal direction due to a characteristic of the hard type material.

Of course, while the waist protecting belt is used in the state wherein the waist support 201 is attached thereto, if a condition of the vertebra-related patient takes a turn for the better, the waist support 201 can be detached from the waist protecting belt, to enable the waist protecting belt to be independently used. Operations when the waist protecting belt is independently used, are as aforementioned above.

As a result, by the detachment type waist protecting belt according to the present invention, advantages are provided in that, since a waist support is provided to the waist protecting belt in such a way as to be selectively attached to the waist protecting belt depending upon a condition of a vertebra-related patient, convenience is increased upon using the waist protecting belt. In this connection, only by possessing the waist protecting belt which is provided with the waist support, it is possible to treat most vertebra-related patients from the beginning to the end.

Moreover, because a portion of each connection ring is positioned in a space which is defined by grooves of a connecting plate and a cover member, rotation of the connection ring is limited to a predetermined angle, whereby it is possible to prevent pulling rods from being entangled one with another. Also, due to the fact that the connecting plates and the cover members are waved, their flexibility is improved, whereby the connecting plates and the cover members can be optimally fitted the contour of the waist of the human body upon wearing the waist protecting belt. Further, since guide rollers and guide pieces are disposed at positions where both ends of the pulling cords are freed through the connecting plates and the cover members, the pulling cords can be easily pulled, and load applied to the pulling cords can he dispersed thereby to lengthen a lifetime of the pulling rods.

In the drawings and specification, there have been disclosed typical preferred embodiments of the invention and, although specific terms are employed, they are used in a generic and descriptive sense only and not for purposes of limitation, the scope of the invention being set forth in the following claims.

What is claimed is:

1. A detachment type waist protecting belt wherein hook and loop fastener strips are attached to distal ends and heightwise middle portions of left and right bands, a pair of connecting plates made of a soft plastic material are secured to proximal ends of the left and right bands, a plurality of connection rings are rotatably fastened to the connecting plates by pins in such a way as to be spaced one from another in a longitudinal direction by a predetermined distance, both ends of a pair of pulling cords respectively pass zigzag from upper and lower ends of the connecting plates through the connection rings so as to be freed at heightwise middle portions of the connecting plates, and a pair of tightening bands are connected to the freed both ends of the pair of pulling cords, characterized in that the detachment type waist protecting belt includes a rigid waist support which has a U-shaped cross-section and which fits a contour of the waist of the human body, guide projections are formed at both sides of an outer surface of the waist support, and the heightwise middle portions of the left and right bands are defined with guide slots which extend in a transverse direction to provide direction for the guide projections, whereby the detachment type waist protecting belt can be equipped with the waist support as occasion arises.

2. The detachment type waist protecting belt as claimed in claim 1, wherein the guide projections are arranged in line along a horizontal direction and each has a head portion and a shaft portion, and circular holes are defined at predetermined locations along the guide slots in a manner such that the head portions of the guide projections are insertable therethrough.

3. The detachment type waist protecting belt as claimed in claim 1, wherein the connecting plates are defined, at places where the connection rings are fastened thereto, with first grooves, a pair of cover members are respectively fastened to the pair of connecting plates and are defined, at places which correspond to the first grooves of the connecting plates, with second grooves, and each first groove and each corresponding second groove cooperate with each other so as to accommodate a portion of the connection ring in a space created therebetween and limit rotation of the connection ring to a predetermined angle; wherein opposite surfaces of the connecting plates and the cover members have a pitch substantially corresponding to the predetermined distance and thereby are rendered flexible for optimal fitting the contour of the waist of the human body; and wherein guide rollers each having a circumferential groove are interposed between the connecting plates and the cover members at positions where the ends of the pulling cords are freed through the connecting plates and the cover members, and guide pieces each having a predetermined height are formed on the cover members in a manner such that they guide the freed ends of pulling cords toward the distal ends of the left and right bands.

* * * * *